US009480856B2

(12) United States Patent
Pravica, Sr.

(10) Patent No.: US 9,480,856 B2
(45) Date of Patent: Nov. 1, 2016

(54) X-RAY TARGETED BOND OR COMPOUND DESTRUCTION

(71) Applicant: The Board of Regents of the Nevada System of Higher Education of Behalf of the University of Nevada, Las Vegas, Las Vegas, NV (US)

(72) Inventor: Michael G. Pravica, Sr., Henderson, NV (US)

(73) Assignee: THE BOARD OF REGENTS OF THE NEVADA SYSTEM OF HIGHER EDUCATION ON BEHALF OF THE UNIVERSITY OF NEVADA, LAS VEGAS, Las Vegas, NV (US)

( * ) Notice: Subject to any disclaimer, the term of this patent is extended or adjusted under 35 U.S.C. 154(b) by 0 days.

(21) Appl. No.: 14/595,431

(22) Filed: Jan. 13, 2015

(65) Prior Publication Data

US 2015/0196777 A1    Jul. 16, 2015

Related U.S. Application Data

(60) Provisional application No. 61/926,528, filed on Jan. 13, 2014.

(51) Int. Cl.
| | |
|---|---|
| A62D 3/174 | (2007.01) |
| A61N 5/10 | (2006.01) |
| G21G 1/02 | (2006.01) |
| B01J 19/12 | (2006.01) |
| H01M 8/06 | (2016.01) |
| A62D 101/02 | (2007.01) |
| A62D 101/06 | (2007.01) |
| A62D 101/22 | (2007.01) |
| A62D 101/26 | (2007.01) |

(52) U.S. Cl.
CPC .............. *A61N 5/10* (2013.01); *A62D 3/174* (2013.01); *B01J 19/125* (2013.01); *G21G 1/02* (2013.01); *H01M 8/0606* (2013.01); *A61N 2005/1098* (2013.01); *A62D 2101/02* (2013.01); *A62D 2101/06* (2013.01); *A62D 2101/22* (2013.01); *A62D 2101/26* (2013.01); *Y02E 60/50* (2013.01)

(58) Field of Classification Search
USPC ........................................................ 422/220
See application file for complete search history.

(56) References Cited

U.S. PATENT DOCUMENTS

2012/0148019 A1* 6/2012 Johnson ............... G01V 5/0016
378/57

FOREIGN PATENT DOCUMENTS

GB        2444310 A  *  6/2008  .............. A61L 2/082

OTHER PUBLICATIONS

Giefers et al., Radiation-induced decomposition of PETN and TATB under pressure, Jun. 22, 2006, Chemical Physics Letters, 429, p. 304-309.*
Wu et al., Ring Closure Mediated by Intramolecular Hydrogen Transfer in the Decomposition of a Push-Pull Nitroaromatic: TATB, Jun. 16, 2000, J. Phys. Chem., 104 (27), p. 6447-6452.*
Romberg et al. Atom-Selective Bond Breaking in a Chemisorbed Homonuclear Molecule Induced by Core Excitation: N2/Ru(001), Jan. 10, 2000, Physical Review Letters, 84 (2), p. 374-377.*
Pravica et al., "A novel method for in situ loading of gases via x-ray induced chemistry," Review of Instruments, 2011, 82, 106102.
Pravica et al., "High Pressure X-ray Diffraction Study of Potassium Chlorate," Journal of Applied Crystallography, 2012, 45, pp. 48-52.
Pravica et al., "Experiments in hard x-ray chemistry: In situ production of molecular hydrogen and x-ray induced combustion," Review of Scientific Instruments 83, 2012, 036102.
Pravica et al., "Hydrazine at High Pressures," Chemical Physics Letters, 2013, 555, pp. 115-118.
Pravica et al., "Measurement of the Energy Dependence of X-ray Induced Decomposition of Potassium Chlorate," Journal of Physical Chemistry, 2013, 117, 2302-2306.
Pravica et al., "High pressure x-ray photochemical studies of carbon tetrachloride: Cl2 production and segregation," Chemical Physics Letters, 2013, vol. 590, 74-76.
Pravica et al., "Studies in useful hard x-ray induced chemistry: Potassium Halates under extreme conditions," Journal of Physics: Conference Series 500, 022009 (2014).
Pravica et al., "X-Ray induced mobility of molecular oxygen at extreme conditions," Applied Physics Letters 103, 224103 (2013).
Akahama et al., "High-pressure Raman spectroscopy of solid oxygen," Phys. Rev. B, 1996, 54(22), pp. 602-605.

(Continued)

*Primary Examiner* — Kevin Joyner
*Assistant Examiner* — Holly Mull
(74) *Attorney, Agent, or Firm* — Michael Best & Friedrich LLP

(57) ABSTRACT

This document provides methods, systems, and devices for inducing a decomposition reaction by directing x-rays towards a location including a particular compound. The x-rays can have an irradiation energy that corresponds to a bond distance of a bond in the particular compound in order to break that bond and induce a decomposition of that particular compound. In some cases, the particular compound is a hazardous substance or part of a hazardous substance. In some cases, the particular compound is delivered to a desired location in an organism and x-rays induce a decomposition reaction that creates a therapeutic substance (e.g., a toxin that kills cancer cells) in the location of the organism. In some cases, the particular compound decomposes to produce a reactant in a reactor apparatus (e.g., fuel cell or semiconductor fabricator).

1 Claim, No Drawings

(56) References Cited

OTHER PUBLICATIONS

Giefers et al., "Radiation-Induced Decomposition of PETN and TATB Under Extreme Conditions," J. Phys. Chem. A, 2008, 112(15), pp. 3352-3359.

Liu et al., "Ruby fluorescence pressure scale: Revisited," Chin. Phys. B, 2013, 22(5) 056201.

Toupry et al., "A Raman spectroscopic study of the structural phase transition and reorientational motions of the ClO4-ions in KClO4," J. Raman Spect., 1983, 14(3), pp. 166-177.

* cited by examiner

X-RAY TARGETED BOND OR COMPOUND DESTRUCTION

CROSS-REFERENCE TO RELATED APPLICATIONS

This application claims the benefit of U.S. Provisional Application Ser. No. 61/926,528, filed Jan. 13, 2014. The disclosure of the prior application is considered part of (and is incorporated by reference in) the disclosure of this application.

FEDERALLY SPONSORED RESEARCH OR DEVELOPMENT

This invention was made with the Department of Energy National Nuclear Security Administration under Award Number(s) DE-NA0000979 and DOE Cooperative Agreement No. DE-FC08-01NV14049 with the University of Nevada, Las Vegas. The Government has certain rights in the invention.

TECHNICAL FIELD

This document relates to methods, systems, and devices for using x-rays to promote desired decomposition reactions. In some cases, methods, systems, and devices provided herein can use hard x-rays having an irradiation energy adapted to break a specific bond in a specific molecule to trigger a desired decomposition reaction.

BACKGROUND

Hazardous substances, such as toxins and explosives, can be used by terrorists to inflict harm on an unsuspecting public. For example, toxins, such as a pathogenic bacteria or chemical agent, could be included in a letter or package and sent to an unsuspecting victim. In addition to the mail recipient(s), these toxins also are potentially dangerous to workers in the sorting room, as mail sorting equipment can cause the release of certain toxins (e.g., spores of Bacillus anthracis). In some cases, inspecting the mail can be hazardous or damaging to the contents of the packages or letters.

Explosives also pose a significant threat to public safety. When an explosive device is identified, a common method of neutralizing the explosive device is to clear the area and explode it with other explosives. Such an explosion, however, can cause significant property damage. Another option for neutralizing an explosive device is to disassemble it physically, but that can require specialized personnel to interact closely with the explosive device and can put specialized personnel at considerable risk.

SUMMARY

Methods, systems, and devices provided herein can include using x-rays to promote desired decomposition reactions. X-rays can have an irradiation energy adapted to trigger a desired decomposition reaction of a particular compound. For example, x-rays can be directed towards a location that possibly includes one or more explosives and/or toxins to trigger decomposition reactions for the explosive(s) and/or toxin(s) to neutralize the explosive(s) and/or toxin(s). In some cases, a desired decomposition reaction can be promoted to produce a desired compound in a desired location. In some cases, x-rays can be used as described herein to promote a desired reaction in a remote or difficult to access location. In some cases, x-rays can be used to release typically gaseous and mobile reactants (e.g., $O_2$, $H_2$, $N_2$, $F_2$, or $Cl_2$) via decomposition reactions of particular compounds, which can provide for a more efficient delivery of reactants.

In some cases, a method provided herein can be used to destroy a hazardous substance. A method of destroying a hazardous substance provided herein can include identifying a location that potentially includes a hazardous substance and directing x-rays towards that location. The hazardous substance can include at least one bond having a bond distance and the x-rays can have an irradiation energy that corresponds to said bond distance in order to induce a decomposition of said hazardous substance by breaking said at least one bond. In some cases, the x-rays can have an irradiation energy of at least 7 keV. In some cases, the x-rays can have an irradiation energy of between 7 keV and 80 keV. In some cases, the x-rays can have an irradiation energy of between 5 keV and 40 keV. In some cases, the x-rays can have an irradiation energy that is equal to $hc/\lambda$, wherein h is the Planck constant, c is the speed of light, and $2\lambda$ is the bond distance or some integral multiple thereof. In some cases, x-rays focused at the location are tuned to the irradiation energy used to break the bond. In some cases, directing x-rays towards the location does not heat the location by more than 50° C., by more than 10° C., by more than 5° C., by more than 2° C., or by more than 1° C. In some cases, the hazardous substance can be an explosive substance and said directing of x-rays towards said location can deactivate or weaken the explosive substance. In some cases, a hazardous substance deactivated by a method, device, or system provided herein, can include an oxidizer having at least one bond and x-rays provided herein can be used to decompose that oxidizer by breaking that bond. For example, $KClO_3$, $KIO_3$, $KBrO_3$, $KClO_4$, and combinations thereof, are suitable oxidizers. Wherein said directing of x-rays towards said location induces an acatalytic decomposition reaction of said oxidizer to produce $O_2$ and KCl. In some cases, the hazardous substance can be TATB and the x-ray irradiation can have an irradiation energy of about 9 keV, or some integer multiple thereof, and used to break a C—C bond in said TATB having a bond distance of about 1.4 Å. In some cases, the hazardous substance is a toxin. For example, a suspected location of a toxin can be a package or envelope. Possible toxins include botulinum toxin, tetanus toxin, staphylococcus, Enterotoxins B, Tricothecenes, Aflatoxin, Anatoxin, Microcystins, Brevetoxin, Saxitoxin, Anthrax, Phosgene, Diphosgene, Ricin, Abrin, Sarin, Tabun, Soman, VX, Sulphur Mustard, Nitrogen Mustards, Lewisites, Hydrogen Cyanide, Cyanogen Chloride, 2-Chloroacetophenone, 2-Chlorobenzilidenemalononitrile, Dibenz (b, f)-1,4-oxazepine, LSD, 3-quinuclidinyl benzilate, Batrachotoxin, Palytoxin, Snake venoms, and combinations thereof.

Methods of treating organisms are also provided herein. In some cases, an organism can be treated by identifying a disease state in a location of said organism and directing x-rays towards that location. The location can include a chemical compound including at least one bond having a bond distance and the x-rays can have an irradiation energy that corresponds to the bond distance in order to induce a decomposition of chemical compound to produce a reaction product. The reaction product can be adapted to kill or weaken cells in said location. In some cases, the x-rays can have an irradiation energy of at least 7 keV. In some cases, the x-rays can have an irradiation energy of between 7 keV and 80 keV. In some cases, the x-rays can have an irradiation energy of between 15 keV and 40 keV. In some cases, the x-rays can have an irradiation energy that is equal to hc/λ, wherein h is the Planck constant, c is the speed of light, and 2λ is the bond distance or some integral multiple of energy. In some cases, directing the x-rays towards the location does not heat the location by more than 50° C. In some cases, directing x-rays towards said location does not heat the location by more than 5° C. The x-rays focused at the location can be tuned to an irradiation energy adapted to break a particular bond. In some cases, a method provided herein can include delivering a chemical compound to a location in an organism and using x-rays to decompose that chemical compound. For example, a delivered chemical compound can be selected from the group consisting of urea, $KClO_3$, $KIO_3$, $KBrO_3$, $KClO_4$, $C_6F_{14}$ (or other fluorocarbon) and combinations thereof. In some cases, a chemical compound can be urea and the reaction product is hydrogen cyanide.

Methods provided herein can include delivering a reactant to a chemical reaction by directing x-rays towards a reactor apparatus. For example, a chemical compound can be placed in a predetermined location and x-rays used to induce a decomposition of the chemical compound to produce a reactant at that predetermined location. The chemical compound can include at least one bond having a bond distance and the x-rays can have an irradiation energy that corresponds to that bond distance. In some cases, the x-rays can have an irradiation energy of at least 7 keV. In some cases, the x-rays can have an irradiation energy of between 7 keV and 80 keV. In some cases, the x-rays can have an irradiation energy of between 15 keV and 40 keV. In some cases, the x-rays can have an irradiation energy that is equal to hc/λ, wherein h is the Planck constant, c is the speed of light, and 2λ is the bond distance or some integral multiple thereof. In some cases, directing the x-rays towards a location in a reactor apparatus does not heat the location by more than 50° C. In some cases, directing the x-rays towards a location in a reactor apparatus does not heat the location by more than 5° C. The x-rays focused at the location can be tuned to an irradiation energy adapted to break a particular bond. In some cases, a method provided herein can include delivering a chemical compound to a particular location. In some cases, a chemical compound can be decomposed to produce $O_2$ or $H_2$. In some cases, the chemical compound can be selected from the group consisting of $NH_3BH_3$, $KClO_3$, $KIO_3$, $KBrO_3$, $KClO_4$, $N_2H_4$, $CCl_4$, $ICl_3$, $C_6F_{14}$, $NaClO_3$, $NaIO_3$, $NaBrO_3$, $NaClO_4$ and combinations thereof. In some case, the reaction apparatus can be a hydrogen fuel cell. In some cases, the reaction apparatus can be a semiconductor fabricator.

Systems provided herein can be adapted to neutralize hazardous substances in packages. A system provided herein, can include an x-ray accelerator (adapted to provide x-rays) having an irradiation energy that corresponds to a bond distance (of a bond in a hazardous substance) in order to induce a decomposition of said hazardous substance by breaking said bond and a conveyor adapted to move packages past the x-ray accelerator to expose the contents of said packages to the x-rays. In some cases, the packages can include envelopes.

Systems provided herein can be adapted to contain a nuclear reactor. In some cases, a substance is included in the nuclear facility and adapted to decompose to produce one or more neutron-moderating gases when exposed to gamma and x-rays from the reactor. The substance can be positioned in the nuclear facility so that said one or more neutron-moderating gases flow to the reactor core. For example, the substance can be $NH_3BH_3$ and it can decompose to release $H_2$ when exposed to x-rays provided herein. In some cases, the one or more neutron-moderating gases include boron, hydrogen, or a combination thereof. The details of one or more embodiments are set forth in the accompanying description below. Other features and advantages will be apparent from the description, drawings, and the claims.

DETAILED DESCRIPTION

Methods, systems, and devices provided herein can include using x-rays to promote desired decomposition reactions. In some cases, penetrating and/or energetic hard x-rays can be used to trigger a decomposition reaction of a hazardous substance. In some cases, penetrating and/or energetic hard x-rays can be used to trigger a decomposition reaction to deliver a desired compound to a desired location. For example, penetrating and/or energetic hard x-rays can be used to trigger a decomposition reaction of a molecule within an organism to produce a therapeutic agent that treats the organism. In some cases, penetrating and/or energetic hard x-rays can be used to release typically gaseous and mobile reactants (e.g., $O_2$, $H_2$, $N_2$, $Cl_2$, $F_2$ or a combination thereof) via decomposition reactions. In some cases, x-ray induced reactions can be triggered with a minimal input of heat and/or without the presence of catalysts. In some cases, penetrating and/or energetic hard x-rays can initiate decomposition reactions in compounds subjected to high pressures. In some cases, penetrating and/or energetic hard x-rays can initiate decomposition reactions in compounds subject to pressures between 0.1 GPa and 20 GPa. In some cases, penetrating and/or energetic hard x-rays can initiate decomposition reactions in compounds at an ambient pressure. In some cases, the methods, systems, and devices provided herein can include using x-rays to induce reactions in sealed or isolated regions of a sample or device. In some cases, the methods, systems, and devices provided herein can include using x-rays to induce reactions from a distance of greater than 10 cm, 1 meter, or 10 meters, depending on the thickness of air, energy of the incident x-rays, and on the chemical composition (e.g. metal or concrete) and thickness of any confining barriers.

In some cases, the methods, systems, and devices provided herein can be used to induce the release of reactant gases and cause crystalline damage, fractures, and/or dislocations that further enhance the molecular diffusion of the gasses, thus improving the diffusion and delivery of reactant gasses throughout a sample or device. For example, the methods, systems, and devices provided herein can be used to open channels for small molecules or reactant gasses to diffuse into deep (e.g., greater than 2 microns, greater than 5 microns, greater than 10 microns, or greater than 100 microns) and/or isolated regions of a sample. In another example, the diffusion of reactant gasses into a deep region of a semiconductor device being manufactured can result in the production of dopant layers or adhesion layers.

X-Rays:

Methods, systems, and devices provided herein can use x-rays adapted to break a specific bond in a specific compound. In some cases, the x-rays can be hard x-rays (i.e., x-rays having an irradiation energy greater than about 7 keV). In some cases, x-rays used in the methods, systems, and devices provided herein can have irradiation energies of between 7 keV and 80 keV. In some cases, x-rays used in the methods, systems, and devices provided herein can have irradiation energies of between 15 keV and 40 keV.

X-rays used in the methods, systems, and devices provided herein can be produced in any appropriate manner. In some cases, the methods, systems, and devices provided herein can produce x-rays using an accelerator (e.g., from Varian) to produce x-rays which irradiate the samples of interest. In some cases, irradiation energy of the x-rays can be selected or varied to tune the irradiation energy to be resonant with standing waves within the unit cell of the solid that enhance absorption within bonds of the molecule and cause chemical decomposition of the target molecule/compound. In some cases, a decomposition reaction can produce gas and/or other inert or toxic products.

In some cases, x-rays used in the methods, systems, and devices provided herein can have an irradiation energy near $E=hc/\lambda$, where h is the Planck constant, c is the speed of light, and $2\lambda$ is any characteristic, repeated distance to create standing waves within the unit cell such as a bond distance of a selected bond that the decomposition reaction seeks to break. In some cases, irradiation energies for x-rays used to trigger a desired decomposition reaction can be empirically determined via experiment. For example, experiments can measure the decomposition rate as a function of irradiation energy to find irradiation energy used in a method, system, or device provided herein. Using tuned irradiation energies for x-rays used in methods, systems, and devices provided herein can enhance the efficiency of the chosen decomposition reaction(s) by choosing energies that maximize the decomposition/absorption-of-energy rate. In some cases, the methods, systems, and devices provided herein can produce a decomposition reaction acatalytically and with little or no introduction of heat. In some cases, the methods provided herein can produce a temperature increase at the location of a decomposition reaction of less than 50° C., less than 25° C., less than 10° C., less than 5° C., or less than 1° C. In some cases, heat can accelerate dangerous reactions that result in undesired chemical reactions, which may even cause an explosion, whereas a method provided herein can break down desired compounds in a controlled fashion with a limited external introduction of heat.

Applications:

Neutralizing Hazardous Substances

Methods, systems, and devices provided herein can use x-rays to neutralize safely hazardous substances, such as explosives and toxins. In some cases, methods, systems, and devices provided herein can use x-rays that can penetrate metal, paper, wood, plastic, and/or ceramics to trigger a decomposition reaction that can neutralize one or more hazardous substances. As discussed above, methods, systems, and devices provided herein can use x-rays having energies tuned to induce the breaking of a particular bond in a particular compound. As discussed above, methods, systems, and devices provided herein can induce decomposition reactions without the presence of a catalyst. As discussed above, methods, systems, and devices provided herein can induce decomposition reactions with a limited temperature increase (e.g., an increase that is less than 50° C., less than 25° C., less than 10° C., less than 5° C., or less than 1° C.

In some cases, methods, systems, and devices provided herein can direct x-rays towards packages, envelopes, or other postal items to target specific toxins that may be present in the mail. In some cases, a system provided herein can include a conveyor belt that carries packages or envelopes past an x-ray accelerator to deliver x-rays towards each package or envelop to induce a decomposition reaction of one or more toxins if those toxins are present. For example, x-rays can be tuned to trigger a decomposition reaction that can neutralize anthrax and spores of Bacillus anthracis. In some cases, x-rays used in methods, systems, and devices provided herein can be tuned to trigger a decomposition reaction in one or more of the following toxins or hazardous materials: Botulinum toxin, Tetanus toxin, Staphylococcus toxins, Enterotoxins B, Tricothecenes, Aflatoxin, Anatoxin, Microcystins, Brevetoxin, Saxitoxin, Anthrax, Phosgene, Diphosgene, Ricin, Abrin, Sarin, Tabun, Soman, VX, Sulphur Mustard, Nitrogen Mustards, Lewisites, Hydrogen Cyanide, Cyanogen Chloride, 2-Chloroacetophenone, 2-Chlorobenzilidenemalononitrile, Dibenz (b, f)-1,4-oxazepine, LSD, 3-quinuclidinyl benzilate, Batrachotoxin, Palytoxin, and Snake venoms. In some cases, methods, systems, and devices provided herein can target phosgene, a nerve toxin, by targeting a C—Cl bond having a bond distance of about 1.74 Å by irradiating a location suspected of having phosgene (e.g., a letter or package) with x-rays having an irradiation energy of about 14 keV. The use of x-rays tuned to induce a decomposition reaction can permit the neutralizing of toxins potentially in packages or envelopes without causing significant damage to other desired contents of the package or envelope. Unlike neutron irradiation methods, directing x-rays towards a package or letter does not cause the package or letter to become radioactive. Additionally, methods, systems, and devices provided herein can neutralize toxins without opening the packages or envelopes and/or prior to sorting the packages or envelopes.

Explosive devices also can pose a threat to public safety. Methods, systems, and devices provided herein can neutralize explosive devices from a safe distance without causing the explosive device to explode. In some cases, explosive devices can include TATB, which includes a carbon-carbon bond having a bond distance of about 1.4 Å. In this case, a method, system, or device provided herein can direct x-rays tuned to an irradiation energy of about 18 keV (to maximize decomposition efficiency) towards such an explosive device to break that carbon-carbon bond and neutralize the TATB explosive. In some cases, explosive devices can include inorganic oxidizers such as $KClO_3$, $KIO_3$, $KBrO_3$, $KClO_4$, $N_2H_4$, $CCl_4$, $NaClO_3$, $NaIO_3$, $NaBrO_3$, and/or $NaClO_4$ which can help drive an explosive reaction. In these cases, a method, system, or device provided herein can direct x-rays tuned to an irradiation energy adapted to drive a decomposition reaction of those oxidizers to detonate or slowly decompose (depending on the x-ray flux) and thus, at least partially, disable an explosive device. In some cases, oxygen can be a key component of explosive chemical reactions. While a rapid release of oxygen may cause detonation in some explosive devices, a slower release of oxygen in some explosive devices can deflagrate or just decompose the explosive device. Accordingly, in some cases, methods provided herein can use x-ray flux and energy to chemically control a decomposition reaction in an explosive device.

Therapeutic Applications

Methods, systems, and devices provided herein can, in some cases, use x-rays to trigger a decomposition reaction of a molecule within an organism to produce a therapeutic agent that treats the organism. In some cases, cancer can be treated by introducing an inert or low toxicity substance capable of releasing a substance toxic to cancer cells upon irradiation. In some cases, the x-rays and/or the inert or low toxicity substance can be directed towards and/or isolated in cancerous tissue. For example, urea can be irradiated with x-rays to decompose the urea into decomposition products that can treat cancer cells. In some cases, it may be possible to decompose urea to form hydrogen cyanide and other residues. Hydrogen cyanide is toxic to cells and can kill cancer cells that have imbibed the urea in a targeted, focused, or controlled fashion. The release of a gas under Room Temperature and Pressure (RTP) conditions can help remove peripheral cancer cells. For example, penetrating and energetic hard x-rays can be used to trigger a decomposition reaction of a molecule within an organism to produce a therapeutic agent that treats the organism. In some cases, oxygen producing reactions, such as $2KClO_3 + h\nu$ (15 keV)$\rightarrow 2KCl + 3O_2$ and $KClO_4 + h\nu \rightarrow KCl + 2O_2$, can be used to release oxygen within cancer cells, which can kill cancer cells and cells on the periphery of tumors due to diffusion of molecular oxygen once produced reducing damage to healthy tissue. Thus, $KClO_3$ or $KClO_4$ can be introduced in solution up to a safe concentration and will be imbibed by cells. In some cases, irradiation of selected regions/tumors within organisms can release oxygen, which is generally toxic to cancer cells and may kill them. In some cases, oxygen can diffuse outward from a tumor and eradicate tumor cells on the periphery of the tumor, which can be more difficult to kill or remove by conventional methods such as surgery.

Nuclear Applications

Methods, systems, and devices provided herein can, in some cases, use x-rays to trigger a release of neutron-moderating gases. In some cases, released neutron-moderating gases can include light elements such as boron and/or hydrogen. In some cases, a container containing a powder such as $NH_3BH_3$ can be placed in nuclear facility and irradiated with x-rays to decompose the $NH_3BH_3$ to release $H_2$. In some cases, if a reactor core begins to meltdown, a large increase in gamma and x-rays from the reactor can cause a release of gas upward into the reactor core, which may reduce the neutron flux and thus reduce (at least temporarily) the chances for meltdown. In some cases, method of neutron mitigation provided herein can be completely passive, without dependence on machines, mechanical or electrical controls.

Delivering Reactants

Methods, systems, and devices provided herein can provide a rapid release and diffusion of reactant gases, which can be used in further reactions or in reactors. For example, methods, systems, and devices provided herein can use x-rays in the 7-30 keV energy range to decompose ammonia borane ($NH_3BH_3$) to release molecular hydrogen, which can be used in a fuel cell. In some cases, systems and devices provided herein can include fuel cells that include ammonia borane and an x-ray generating accelerator or x-ray tube adapted to provide x-rays towards the ammonia borane to produce hydrogen used by the fuel cell to produce electricity. In some cases, a fuel cell provided herein can include $KClO_3$, $KIO_3$, $KBrO_3$, $KClO_4$, $N_2H_4$, $CCl_4$, $NaClO_3$, $NaIO_3$, $NaBrO_3$, and/or $NaClO_4$ and an accelerator adapted to provide x-rays towards the $KClO_3$, $KIO_3$, $KBrO_3$, $KClO_4$, $N_2H_4$, $CCl_4$, $NaClO_3$, $NaIO_3$, $NaBrO_3$, and/or $NaClO_4$ to trigger a decomposition reaction to produce molecular oxygen as a reactant gas. The use of x-rays in methods, systems, and devices provided herein can produce $O_2$ and $H_2$ within a few seconds (e.g., less than 10 seconds, less than 5 seconds, less than 2 seconds) in order to deliver reactant gases quickly to a fuel cell. The x-ray induced release of gases, crystalline damage, fractures, dislocations, or a combination thereof can aid molecular diffusion and, thus, the diffusion and delivery of reactants throughout a sample.

In some cases, a reactor device provided herein can be a semiconductor fabricator and x-rays can be used to deliver reactants to select areas of a semiconductor device under production. For example, select compounds can be irradiated with x-rays to decompose to yield reactants to drive reactions that enhance adhesion of dissimilar, stressed, and/or sandwiched surfaces (e.g., layers of semiconductors that form p-n junctions). Methods, systems, and devices provided herein can open channels for small molecules or reactant gasses to diffuse into deep (e.g., greater than 2 microns, greater than 5 microns, or greater than 10 microns) and/or isolated regions of a semiconductor device being fabricated. For example, the diffusion of reactant gasses into a deep region of a semiconductor device being manufactured can result in the production of dopant layers or adhesion layers. In some cases, additional reactions using reactants produced using x-ray decomposition methods provided herein can produce GaN in a semiconductor device. Oxygen or other gases released inside the semiconductor using these methods may be used as a novel means to carry current.

What is claimed is:

1. A method of destroying a hazardous substance comprising:
   a. identifying a location that potentially comprises a hazardous substance, said hazardous substance comprising at least one bond having a bond distance; and
   b. directing x-rays towards said location, the x-rays having an irradiation energy that corresponds to said bond distance in order to induce a decomposition of said hazardous substance by breaking said at least one bond;
   wherein said hazardous substance is an explosive substance and said directing of x-rays towards said location does not cause an explosion;
   wherein said hazardous substance comprises an oxidizer comprising said at least one bond, wherein said oxidizer is selected from $KClO_3$, $KIO_3$, $KBrO_3$, $KClO_4$, fluorocarbons and combinations thereof, wherein said directing of x-rays towards said location induces an acatalytic decomposition reaction of said oxidizer to produce at least $O_2$, wherein said hazardous substance comprises TATB, and wherein said x-ray has an irradiation energy of about 9 keV and is used to break a C—C bond in said TATB having a bond distance of about 1.4 Å.

* * * * *